(12) United States Patent
Flohr

(10) Patent No.: US 7,166,356 B2
(45) Date of Patent: Jan. 23, 2007

(54) SUPERABSORBENT POLYMERS HAVING RADIATION ACTIVATABLE SURFACE CROSS-LINKERS AND METHOD OF MAKING THEM

(75) Inventor: Andreas Flohr, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 84 days.

(21) Appl. No.: 10/911,302

(22) Filed: Aug. 4, 2004

(65) Prior Publication Data

US 2005/0032936 A1   Feb. 10, 2005

(30) Foreign Application Priority Data

Aug. 6, 2003   (EP) .................. 03017940
Nov. 22, 2003  (EP) .................. 03026798
Jul. 21, 2004  (EP) .................. 04017153

(51) Int. Cl.
  *B32B 5/16*   (2006.01)
  *A61F 13/515* (2006.01)

(52) U.S. Cl. ............... 428/403; 428/323; 428/327; 428/407; 604/367; 604/372

(58) Field of Classification Search ........... 428/403, 428/407, 327; 604/367, 372
See application file for complete search history.

(56) References Cited

U.S. PATENT DOCUMENTS

| | | | |
|---|---|---|---|
| 3,214,492 A | 10/1965 | Tocker | |
| 3,429,852 A | 2/1969 | Skoultchi | |
| 3,622,848 A | 11/1971 | Hendrix et al. | |
| 3,661,875 A | 5/1972 | Sieja | |
| 4,043,887 A * | 8/1977 | Pacifici et al. | ........... 522/45 |
| 4,062,817 A | 12/1977 | Westerman | |
| 4,076,663 A | 2/1978 | Masuda et al. | |
| 4,093,776 A | 6/1978 | Aoki et al. | |
| 4,304,895 A | 12/1981 | Loshaek | |
| 4,666,983 A | 5/1987 | Tsubakimoto et al. | |
| 4,734,478 A | 3/1988 | Tsubakimoto et al. | |
| 4,922,004 A | 5/1990 | Köhler et al. | |
| 5,248,805 A | 9/1993 | Boettcher et al. | |
| 5,597,873 A * | 1/1997 | Chambers et al. | ........ 525/330.1 |
| 5,633,316 A * | 5/1997 | Gartner et al. | ........... 525/54.32 |
| 5,859,084 A * | 1/1999 | Schroder et al. | ........... 522/34 |
| 5,922,417 A | 7/1999 | Singleton et al. | |
| 5,976,696 A * | 11/1999 | Collette et al. | ........... 428/407 |
| 6,007,833 A * | 12/1999 | Chudzik et al. | ........... 424/425 |

(Continued)

FOREIGN PATENT DOCUMENTS

EP   0 279 475 A2   8/1988

(Continued)

*Primary Examiner*—H. Thi Le
(74) *Attorney, Agent, or Firm*—Edward Milbrada; Eric T. Addington; John G. Powell

(57) ABSTRACT

The present invention relates to superabsorbent polymer particles with improved surface cross-linking and their use in absorbent articles.

The superabsorbent polymer particles of the present invention comprise a water-absorbing resin and the reaction product of a radiation activatable surface cross-linker wherein the reaction product of the radiation activatable surface cross-linker is present at surfaces of the superabsorbent polymer particles. The radiation activatable surface cross-linker comprises at least two radiation activatable groups R, which are covalently bound to each other or to at least one spacer group S.

Moreover, the invention relates to a process for making these superabsorbent polymer particles.

8 Claims, 2 Drawing Sheets

U.S. PATENT DOCUMENTS

| | | | |
|---|---|---|---|
| 6,222,091 B1 * | 4/2001 | Beihoffer et al. | 604/368 |
| 6,376,072 B1 * | 4/2002 | Evans et al. | 428/370 |
| 6,455,600 B1 | 9/2002 | Hähnle et al. | |
| 6,565,981 B1 | 5/2003 | Messner et al. | |
| 6,803,107 B2 * | 10/2004 | Mitchell et al. | 428/403 |
| 2003/0135172 A1 | 7/2003 | Whitmore et al. | |
| 2004/0137250 A1 | 7/2004 | Daniel et al. | |
| 2004/0140070 A1 | 7/2004 | Ponomarenko et al. | |
| 2004/0155383 A1 | 8/2004 | Jackson et al. | |
| 2005/0142965 A1 | 6/2005 | LaFortune | |

FOREIGN PATENT DOCUMENTS

| | | |
|---|---|---|
| EP | 0 700 673 A1 | 3/1996 |
| JP | 1-292103 | 11/1989 |
| WO | WO 81/03274 A1 | 11/1981 |

* cited by examiner

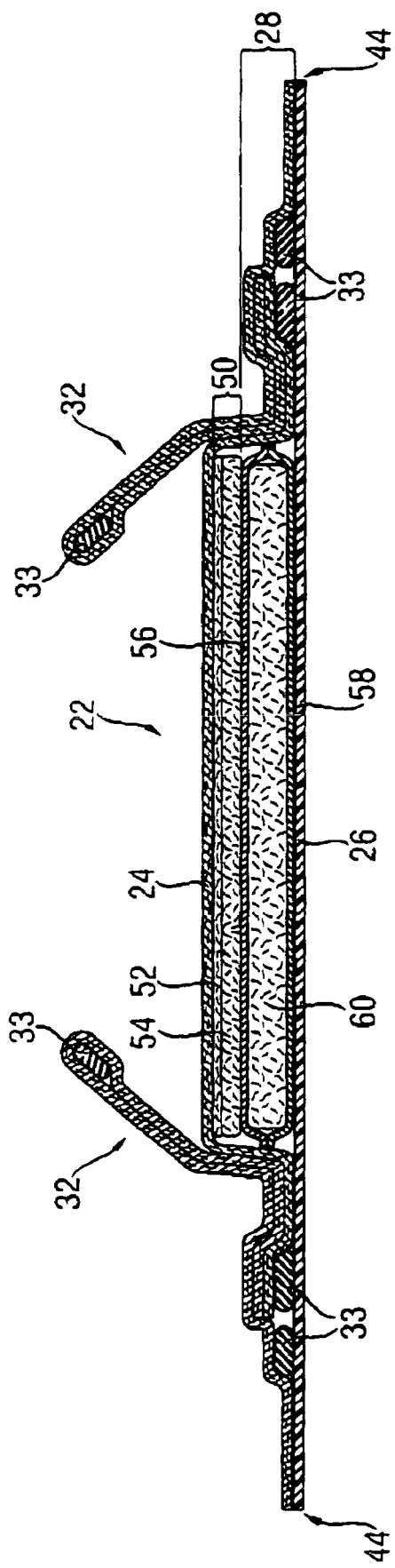

SUPERABSORBENT POLYMERS HAVING RADIATION ACTIVATABLE SURFACE CROSS-LINKERS AND METHOD OF MAKING THEM

FIELD OF THE INVENTION

The present invention relates to superabsorbent polymer particles with improved surface cross-linking and their use in absorbent articles.

Moreover, the invention relates to a process for making these superabsorbent polymer particles.

BACKGROUND OF THE INVENTION

Superabsorbent polymers (SAPs) are well known in the art. They are commonly applied in absorbent articles, such as diapers, training pants, adult incontinence products and feminine care products to increase the absorbent capacity of such products while reducing their overall bulk. The SAPs generally are capable of absorbing and retaining amounts of aqueous fluids equivalent to many times their own weight.

Commercial production of SAPs began in Japan in 1978. The early superabsorbent was a cross-linked starch-g-polyacrylate. Partially neutralized polyacrylic acid eventually replaced earlier superabsorbents in the commercial production of SAPs, and is the primary polymer employed for SAPs today. SAPs are often applied in form of small particles, such as fibers or granules. They generally consist of a partially neutralized lightly cross-linked polymer network, which is hydrophilic and permits swelling of the network once submerged in water or an aqueous solution such as physiological saline. The cross-links between the polymer chains assure that the SAP does not dissolve in water.

After absorption of an aqueous solution, swollen SAP particles become very soft and deform easily. Upon deformation the void spaces between the SAP particles are blocked, which drastically increases the flow resistance for liquids. This is generally referred to as "gel-blocking". In gel blocking situations liquid can move through the swollen SAP particles only by diffusion, which is much slower than flow in the interstices between the SAP particles.

One commonly applied way to reduce gel blocking is to make the particles stiffer, which enables the SAP particles to retain their original shape thus creating or maintaining void spaces between the particles. A well-known method to increase stiffness is to cross-link some of the carboxyl groups exposed on the surface of the SAP particles. This method is commonly referred to as surface cross-linking.

The art refers, e.g., to surface cross-linked and surfactant coated absorbent resin particles and a method of their preparation. The surface cross-linking agent can be a polyhydroxyl compound comprising at least two hydroxyl groups, which react with the carboxyl groups on the surface of the SAP particles. In some art, surface cross-linking is carried out at temperatures of 150° C. or above. The particles are preferably exposed to the elevated temperatures for at least 5 minutes but less than 60 minutes.

A water-soluble peroxide radical initiator as a surface cross-linking agent is also known. An aqueous solution containing the surface cross-linking agent is applied on the surface of the polymer. The surface cross-linking reaction is achieved by heating to a temperature such that the peroxide radical initiator is decomposed while the polymer is not decomposed.

More recently the use of an oxetane compound and/or an imidazolidinone compound as a surface cross-linking agent has been disclosed. The surface cross-linking reaction can be carried out under heat, wherein the temperature is preferably in the range of 60° C. to 250° C. Alternatively, the surface cross-linking reaction can also be achieved by a photo-irradiation treatment, preferably using ultraviolet rays.

In general, the surface cross-linking agent is applied on the surface of the SAP particles. Therefore, the reaction preferably takes place on the surface of the SAP particles, which results in improved cross-linking on the surface of the particles while not substantially affecting the core of the particles. Hence, the SAP particles become stiffer and gel-blocking is reduced.

A drawback of the commercial surface cross-linking process described above is that it takes relatively long, commonly at least about 30 min. However, the more time is required for the surface cross-linking process, the more surface cross-linking agent will penetrate into the SAP particles, resulting in increased cross-linking inside the particles, which has a negative impact on the capacity of the SAP particles. Therefore, it is desirable to have short process times for surface cross-linking. Furthermore, short process times are also desirable with respect to an overall economic SAP particle manufacturing process.

Another drawback of common surface cross-linking processes is that they take place only under relatively high temperatures, often around 150° C. or above. At these temperatures, not only the surface cross-linker reacts with the carboxyl groups of the polymer, but also other reactions are activated, e.g., anhydride-formation of neighboring carboxyl groups within or between the polymer chains, and dimer cleavage of acrylic acid dimers incorporated in the SAP particles. Those side reactions also affect the core, decreasing the capacity of the SAP particles. In addition, exposure to elevated temperatures can lead to color degradation of the SAP particles. Therefore, these side reactions are generally undesirable.

SAPs known in the art are typically partially neutralized, e.g., with sodium hydroxide. However, neutralization has to be carefully balanced with the need for surface cross-linking: The surface cross-linking agents known in the art only react with free carboxyl groups comprised by the polymer chains but they are not able to react with a neutralized carboxyl groups. Thus, the carboxyl groups can either be applied for surface cross-linking or for neutralization, but the same carboxyl group cannot be applied to fulfill both tasks. Surface cross-linking agents known in the art do not react with chemical groups other than carboxyl groups, e.g., they do not react with aliphatic groups.

In the process of making SAP particles, neutralization of free carboxyl groups typically comes first, before surface cross-linking takes place. Indeed, the neutralization step is often carried out in the very beginning of the process, before the monomers are polymerized and cross-linked to form the SAP. Such a process is named 'pre-neutralization process'. Alternatively, the SAP can be neutralized in the middle of polymerization or after polymerization ('post-neutralization'). Furthermore, a combination of these alternatives is also possible.

As the overall number of free carboxyl groups on the outer surface of the SAP particles is limited by the foregoing neutralization, it is very difficult to obtain particles with a high degree of surface cross-linking and hence, a high stiffness to reduce gel-blocking. Furthermore, it is very difficult to obtain SAP particles with evenly distributed surface cross-linking, as the remaining free carboxyl groups are not only few in number but generally also randomly distributed, which sometimes results in SAP particles with regions of rather dense surface cross-linking and regions of sparsely surface cross-linking.

It is therefore an objective of the present invention to provide SAP particles, which have a high degree of surface cross-linking and at the same time allow for a high degree of neutralization.

It is a further objective of the present invention to provide SAP particles with evenly distributed, homogenous surface cross-linking.

Furthermore, it is an objective of the present invention to provide a process to produce SAP particles with the above-mentioned advantages.

It is a still further objective of the present invention to provide a process to produce SAP particles, wherein the process step of surface cross-linking can be carried out quickly to increase the efficiency of the process.

Moreover, a further objective of the present invention is to provide a process to produce SAP particles, which can be carried out at moderate temperatures in order to reduce undesired side reactions, such as anhydride-formation and dimer cleavage.

SUMMARY OF THE INVENTION

The present invention relates to superabsorbent polymer particles comprising a water-absorbing resin and the reaction product of a radiation activatable surface cross-linker wherein the reaction product of the radiation activatable surface cross-linker is present at surfaces of the superabsorbent polymer particles. The radiation activatable surface cross-linker comprises at least two radiation activatable groups $R_1$ and $R_2$, which are covalently bound to each other or to at least one spacer group S.

The spacer group S is selected from the group consisting of an organic group with a molecular weight of up to Mw=10,000, and a polymeric group with a molecular weight of up to Mw=1,000,000. As used herein, the term "molecular weight" or "Mw", when used in reference to a polymeric material, refers to the weight average molecular weight thereof.

The radiation activatable groups $R_1$ and $R_2$ are the same or different and are selected from the group consisting of acetophenone, benzophenone, anthraquinone, xanthone, thioxanthone, camphorquinone, terephthalophenone, benzil, fluorenone, -ketocoumarin, acetophenone-, benzophenone-, anthraquinone-, xanthone-, thioxanthone-, camphorquinone-, terepnthalophenone-, benzil-, fluorenone- and -ketocoumarin-derivatives. Suitable acetophenone derivatives or benzophenone derivatives, for example, also comprise reaction products, such as condensation products, of acetophenone derivatives or benzophenone derivatives, comprising at least two acetophenone or benzophenone groups. In a preferred embodiment of the invention, derivatized radiation activatable groups $R_1$ and $R_2$ are used to enable or further enhance water-solubility.

Alternatively, the radiation activatable groups $R_1$ and $R_2$ are the same or different and comprise a group comprising a first group selected from the group consisting of methyl, benzyl, aryl, preferably phenyl and substituted phenyl, and a second group selected from the group consisting of an aryl, an alkyl of 1 to 4 carbon atoms, cyclopropyl, cyclopentyl, cyclohexyl, α,α-dialkoxyalkyl, and α-hydroxyalkyl and wherein the first group is covalently bound to the second group via an additional carbonyl group, and wherein the second group is covalently bound to the spacer group S.

The radiation activatable surface cross-linker comprises either only one kind of radiation activatable group or comprises two or more different radiation activatable groups. The radiation activatable surface cross-linker comprises optionally either only one kind of spacer group S or comprises two or more different spacer groups S.

The present invention further relates to a method of making superabsorbent polymer particles which comprises the steps of
 a) providing a water-absorbing resin
 b) adding radiation activatable surface cross-linkers
 c) exposing said water-absorbing resin and said radiation activatable surface cross-linkers to electromagnetic irradiation
wherein the radiation activatable surface cross-linker is a radiation activatable surface cross-linker as described above.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 2 is a cross-sectional view of the disposable diaper shown in FIG. 1

DETAILED DESCRIPTION OF THE INVENTION

Figure 1:
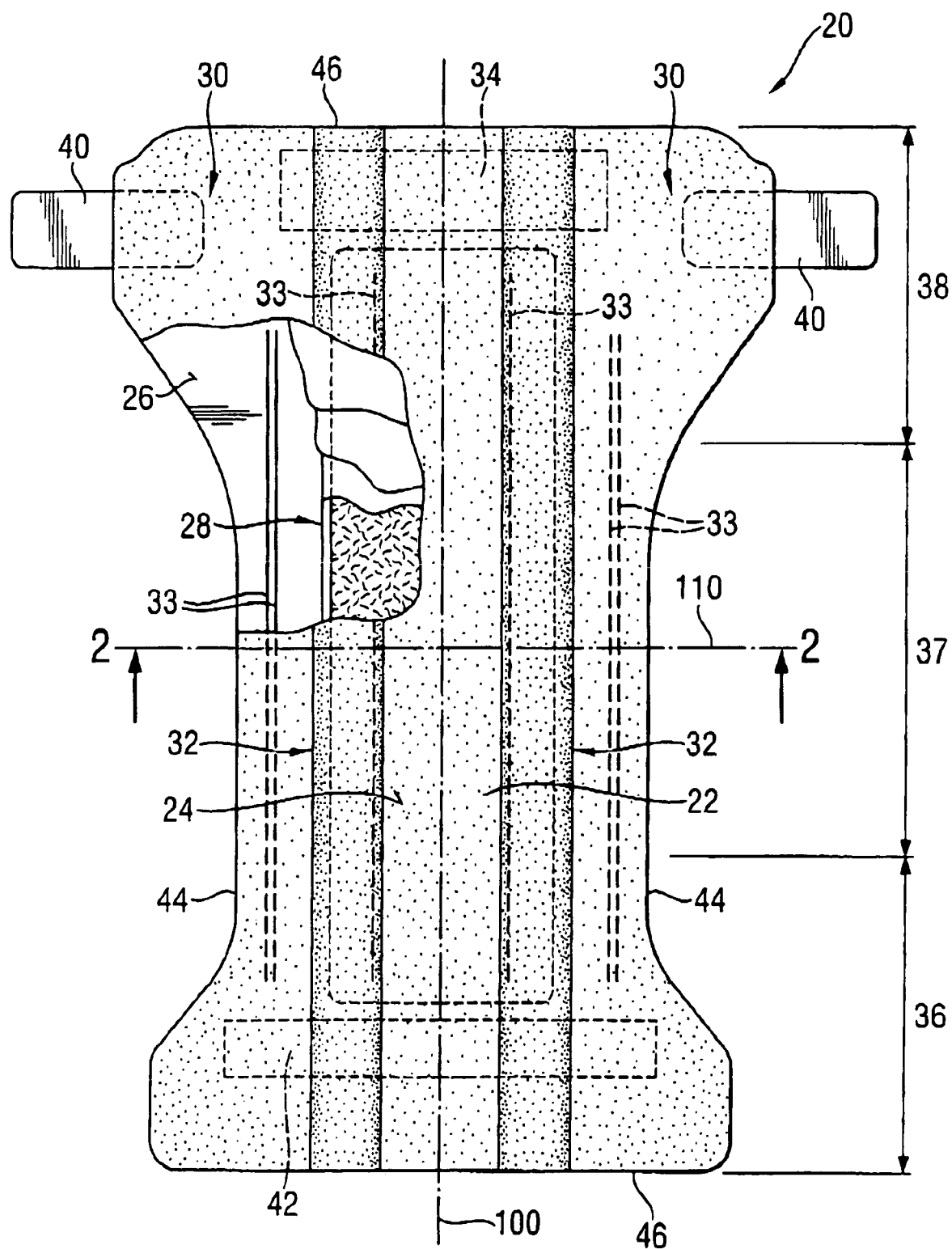
FIG. 1 is a top plan view of a disposable diaper, with the upper layers partially cut away.

The SAPs according to the present invention comprise a homopolymer of partially neutralized α,β-unsaturated carboxylic acid or a copolymer of partially neutralized α,β-unsaturated carboxylic acid copolymerized with a monomer copolymerizable therewith. Furthermore, the homo-polymer or copolymer comprised by the SAP comprises aliphatic groups, wherein at least some of the aliphatic groups are at least partially exposed on the surface of the superabsorbent polymer particles SAPs are available in a variety of chemical forms, including substituted and unsubstituted natural and synthetic polymers, such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, SAPs useful herein have a multiplicity of anionic, functional groups, such as sulfonic acid, and more typically carboxyl groups. Examples of polymers suitable for use herein include those, which are prepared from polymerizable, unsaturated, acid-containing monomers. Thus, such monomers include the olefinically unsaturated acids and anhydrides that contain at least one carbon-to-carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing SAPs. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 and in U.S. Pat. No. 4,062,817.

Olefinically unsaturated carboxylic acid and carboxylic acid anhydride monomers include the acrylic acids typified by acrylic acid itself, methacrylic acid, ethacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred SAPs according to the present invention contain carboxyl groups. These polymers comprise hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid, partially neutralized polymethacrylic acid, and slightly network crosslinked polymers of partially neutralized polymethacrylic acid. These polymers can be used either solely or in the form of a mixture of two or more different polymers, that when used as mixtures, individually do not have to be partially neutralized, whereas the resulting copolymer has to be. Examples of these polymer materials are disclosed in U.S. Pat. Nos. 3,661,875, 4,076,663, 4,093,776, 4,666,983, and 4,734,478.

Most preferred polymer materials for use herein are slightly network crosslinked polymers of partially neutralized polyacrylic acids, slightly network crosslinked polymers of partially neutralized polymethacrylic acids, their copolymers and starch derivatives thereof. Most preferably, SAPs comprise partially neutralized, slightly network crosslinked, polyacrylic acid (i.e., poly (sodium acrylate/acrylic acid)). Preferably, the SAPs are at least 50%, more preferably at least 70%, even more preferably at least 75% and even more preferably from 75% to 95% neutralized. Network cross-linking renders the polymer substantially water-insoluble and, in part, determines the absorptive capacity of the hydrogel-forming absorbent polymers. Processes for network cross-linking these polymers and typical network cross-linking agents are described in greater detail in U.S. Pat. No. 4,076,663.

A suitable method for polymerizing the α,β-unsaturated carboxylic acid monomers is aqueous solution polymerization, which is well known in the art. An aqueous solution comprising α,β-unsaturated carboxylic acid monomers and polymerization initiator is subjected to a polymerization reaction. The aqueous solution may also comprise further monomers, which are co-polymerizable with the α,β-unsaturated carboxylic acid monomers. At least the α,β-unsaturated carboxylic acid has to be partially neutralized, either prior to polymerization of the monomers, during polymerization or post polymerization. In a preferred embodiment of the present invention, the monomers (including α,β-unsaturated carboxylic acid monomers and possible comonomers) are at least 50%, more preferably at least 70%, even more preferably at least 75% and even more preferably from 75% to 95% neutralized.

The monomers in aqueous solution are polymerized by standard free radical techniques, commonly by using a photoinitiator for activation, such as ultraviolet (UV) light. Alternatively, a redox initiator may be used. In this case, however, increased temperatures are necessary.

The water-absorbent resin will preferably be lightly cross-linked to render it water-insoluble. The desired cross-linked structure may be obtained by the co-polymerization of the selected water-soluble monomer and a cross-linking agent possessing at least two polymerizable double bonds in the molecular unit. The cross-linking agent is present in an amount effective to cross-link the water-soluble polymer. The preferred amount of cross-linking agent is determined by the desired degree of absorption capacity and the desired strength to retain the absorbed fluid, that is, the desired absorption under load. Typically, the cross-linking agent is used in amounts ranging from 0.0005 to 5 parts by weight per 100 parts by weight of monomers (including α,β-unsaturated carboxylic acid monomers and possible comonomers) used. If an amount over 5 parts by weight of cross-linking agent per 100 parts is used, the resulting polymer has a too high cross-linking density and exhibits reduced absorption capacity and increased strength to retain the absorbed fluid. If the cross-linking agent is used in an amount less than 0.0005 parts by weight per 100 parts, the polymer has a too low cross-linking density and when contacted with the fluid to be absorbed becomes rather sticky, water-soluble and exhibits a low absorption performance, particularly under load. The cross-linking agent will typically be soluble in the aqueous solution.

Alternatively to co-polymerizing the cross-linking agent with the monomers, it is also possible to cross-link the polymer chains in a separate process step after polymerization.

After polymerization, cross-linking and partial neutralization, the viscous SAPs are dehydrated (i.e., dried) to obtain dry SAPs. The dehydration step can be performed by heating the viscous SAPs to a temperature of about 120° C. for about 1 or 2 hours in a forced-air oven or by heating the viscous SAPs overnight at a temperature of about 60° C. The content of residual water in the dehydrated SAP after drying predominantly depends on drying time and drying temperature and can range from 0.5% by weight of dry SAP up to 50% by weight of dry SAP. Preferably, the content of residual water in the dehydrated SAP after drying is 0.5%–45% by weight of dry SAP, more preferably 0.5%–30%, even more preferably 0.5%–15% and most preferably 0.5%–5%.

The SAPs can be transformed into particles of numerous shapes. The term "particles" refers to granules, fibers, flakes, spheres, powders, platelets and other shapes and forms known to persons skilled in the art of SAPs. E.g., the particles can be in the form of granules or beads, having a particle size of about 10 to 1000 μm, preferably about 100 to 1000 μm. In another embodiment, the SAPs can be in the shape of fibers, i.e., elongated, acicular SAP particles. In those embodiments, the SAP fibers have a minor dimension (i.e., diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

According to the present invention the dehydrated SAP particles undergo a surface cross-linking process step. The term "surface" describes the outer-facing boundaries of the particle. For porous SAP particles, exposed internal surfaces may also belong to the surface. The term "surface cross-linked SAP particle" refers to an SAP particle having its molecular chains present in the vicinity of the particle surface cross-linked by a compound referred to as surface cross-linker. The surface cross-linker is applied to the surface of the particle. In a surface cross-linked SAP particle the level of cross-links in the vicinity of the surface of the SAP particle is generally higher than the level of cross-links in the interior of the SAP particle.

Commonly applied surface cross-linkers are thermally activatable surface cross-linkers. The term "thermally activatable surface cross-linkers" refers to surface cross-linkers, which only react upon exposure to increased temperatures, typically around 150° C. Thermally activatable surface cross-linkers known in the prior art are, e.g., di- or poly-functional agents that are capable of building additional cross-links between the polymer chains of the SAPs. Other thermally activatable surface cross-linkers include, e.g., di- or polyhydric alcohols, or derivatives thereof, capable of forming di- or polyhydric alcohols. Representatives of such agents are alkylene carbonates, ketales, and di- or polyglycidylethers. Moreover, (poly)glycidyl ethers, haloepoxy compounds, polyaldehydes, polyoles and polyamines are also well known thermally activatable surface cross-linkers. The cross-linking is based on a reaction between the functional groups comprised by the polymer, for example, an esterification reaction between a carboxyl group (comprised by the polymer) and a hydroxyl group (comprised by the surface cross-linker). As typically a relatively big part of the carboxyl groups of the polymer chain is neutralized prior to the polymerization step, commonly only few carboxyl groups are available for this surface cross-linking process known in the art. E.g. in a 70% percent neutralized polymer only 3 out of 10 carboxylic groups are available for covalent surface cross-linking.

The present invention relates to radiation activatable surface cross-linkers, the SAP particles obtained from such irradiation activated surface cross-linking, methods of preparing such irradiation activated surface cross-linked SAP particles and their use in disposable absorbent articles.

Such radiation activatable surface cross-linkers comprise at least two radiation activatable groups, capable of forming covalent cross-linking bonds upon being impacted by irradiation energy. Radiation activatable compounds as such and their synthesis are know in the art, e.g., from European Patent Application EP-A-0 377 191; U.S. Pat. Nos. 3,214,492; 3,429,852; 3,622,848; 4,304,895; German Patent Application DE-A-3534645 and European Patent Application EP-A-279 475.

In the present invention it was found that radiation activatable compounds could be used as surface cross-linkers comprising at least two radiation activatable groups R, which are covalently bound to each other or to at least one spacer group S. The radiation activatable groups are capable of forming covalent cross-linking bonds upon being impacted by irradiation energy. Moreover, the radiation activatable surface cross-linker can function very well for the surface cross-linking of SAP particles to provide superior capacity and permeability properties.

Formula I shows a preferred embodiment of the radiation activatable surface cross-linker according to the present invention:

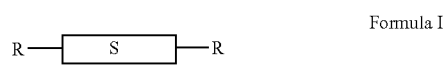

Formula I

Formula II shows another preferred embodiment of the radiation activatable surface cross-linker of the present invention:

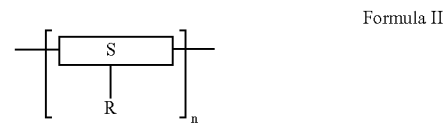

Formula II wherein n is an integer of equal or greater than 2.

In Formula II, and I S denotes a spacer group and R denote radiation activatable groups which are able to form organic radicals.

According to the present invention, the radiation activatable surface cross-linker may comprise only one kind of radiation activatable group R. Alternatively the radiation activatable surface cross-linker may comprise two or more different radiation activatable groups R.

Furthermore, according to the present invention, the radiation activatable surface cross-linker may comprise only one kind of spacer group S. Alternatively the radiation activatable surface cross-linker may comprise two or more different spacer groups S. In another alternative embodiment, the radiation activatable surface cross-linker does not comprise a spacer.

Radiation Activatable Groups R

The radiation activatable groups R are covalently bound to each other or to the spacer group S and can be selected from the group consisting of acetophenone, benzophenone, anthraquinone, xanthone, thioxanthone, camphorquinone, terephthalophenone benzil, fluorenone, α-ketocoumarin, as well as acetophenone-, benzophenone-, anthraquinone-, xanthone-, thioxanthone-, camphorquinone-, terephthalophenone-, benzil-, fluorenone-, and α-ketocoumarin-derivatives. Suitable acetophenone derivatives or benzophenone derivatives, for example, also comprise reaction products, such as condensation products of acetophenone derivatives or benzophenone derivatives, comprising at least two acetophenone or benzophenone groups.

Preferably, the radiation activatable groups R such as acetophenone, benzophenone, anthraquinone, xanthone, thioxanthone, camphorquinone, terephthalophenone, benzil, fluorenone, α-ketocoumarin are derivatized to either enable or further enhance water-solubility.

Particularly preferred radiation activatable groups R are acetophenone- or benzophenone-derivatives.

Even more preferred radiation activatable groups R are the water-soluble derivates of actetophenone and benzophenone.

Suitable acetophenone derivatives or benzophenone derivatives are described, for example, in European Patent Application EP-A-0 346 734; European Patent Application EP-A-0 377 199; European Patent Application EP-A-0 246 848; German Patent Application DE-A-4 037 079 and German Patent Application DE-A-3 844 444.

Preferred acetophenone derivatives and benzophenone derivatives have the general Formula III:

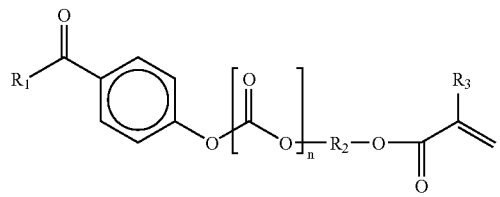

Formula III wherein n is 0 or 1, and $R_1$ is substituted or unsubstituted phenyl or $C_1$–$C_4$-alkyl or an ethylenically unsaturated group, preferably comprising an acrylic or methacrylic group, and $R_2$ is an organic group having from 1 to 100 carbon atoms, which may be interrupted by up to 49 oxygen atoms, and $R_3$ is a hydrogen atom or methyl.

$R_2$ is preferably an organic group having between 4 and 60 carbon atoms, which may be interrupted by between 1 and 29 oxygen atoms, in particular having between 10 and 40 carbon atoms which may be interrupted by between 4 and 19 oxygen atoms.

$R_1$ is particularly preferably methyl or phenyl.

$R_2$ is particularly preferably alkylene, in particular $C_2$–$C_8$-alkylene.

The preferred acetophenone derivatives and benzophenone derivatives according to Formula III can be covalently bound to a spacer group S to form a radiation activatable surface cross-linker as depicted in Formula IV:

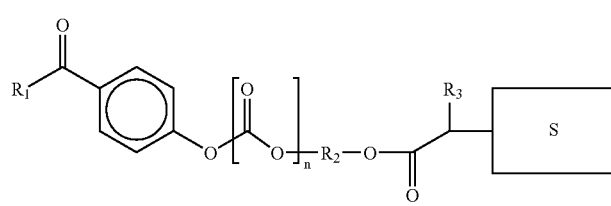

Formula IV

Alternatively, according to the present invention the radiation activatable groups R have the form according to Formula V:

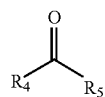

Formula V wherein $R_4$ is selected from the group consisting of methyl, benzyl, aryl, preferably phenyl and substituted phenyl and $R_5$ is selected from the group consisting of an aryl, an alkyl of 1 to 4 carbon atoms, cyclopropyl, cyclopentyl, cyclohexyl, α,α-dialkoxyalkyl, and α-hydroxyalky and wherein $R_5$ is covalently bound to the spacer group S or to another radiation activatable group R.

Two of the radiation activatable groups R according to Formula V can be covalently bound to a spacer group S to form a radiation activatable surface cross-linker as depicted in Formula VI:

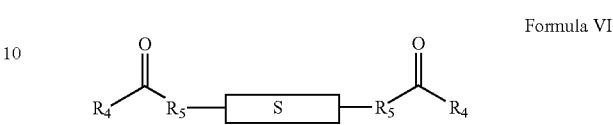

Formula VI

The Spacer Group S

The spacer group S is selected from the group consisting of an organic group and a polymeric group. If the spacer group S is an organic group, the organic group has a molecular weight of up to Mw=10,000, preferably up to 1,000. Alternatively, the spacer group S, for example, comprises up to 100 carbon atoms. If the spacer group S is a polymeric group, the polymeric group has a molecular weight up to Mw=1,000,000, preferably from 5,000 to 600,000, more preferably from 10,000 to 500,000 and particularly preferably from 30,000 to 250,000. If the radiation activatable surface cross-linker comprises a spacer group S, the spacer group S in covalently bound to the radiation activatable groups R.

If the spacer group S is a polymeric group, then such polymer has preferably been build up from free-radical polymerizable compounds (=comonomers). At least 40% by weight of the polymer, particularly preferable at least 60% by weight, very particularly preferable at least 80% by weight, is composed of the comonomers.

Without wishing to be bound by theory, it is believed, that the choice of monomers as well as length and molecular weight of the polymeric spacer S determine (a) the distance of how far the radiation activatable groups $R_1$ and $R_2$ are spaced apart and (b) the rigidity of the polymeric spacer S, which in turn impact on the glass transition temperature $T_g$ of such polymeric spacer S. In a preferred embodiment of the present invention the polymeric spacer S has a glass transition temperature of less than ambient temperature ($T_g$<25° C.) to avoid brittle breaks of such radiation activatable surface cross-linker upon swelling of the superabsorbent polymer.

In a preferred embodiment of the present invention, the comonomers may comprise the following groups as part of a monomer molecule: carboxylic acid, sulfonic acid, phosphonic acid or hydroxyl. Carboxylic and sulfonic acid groups are preferred.

Typical, but not limiting, examples for such preferable monomer-units according to the present invention are:

acrylic acid, methacrylic acid, maleic acid, fumaric acid, itaconic acid, vinylsulfonic acid, allylsulfonic acid, acrylamidomethanpropane sulfonic acid, vinylalcohol, vinylamine, allylamine, polyethyleneglycolemonoacrylate, polyethyleneglycolediacrylate, polyethyleneglycolemonoallyether, polyethyleneglycolediallylether, ethoxylated trimethylolpropane-triacrylate, ethylene, propylene, vinyl chloride, aziridine, isobutylene, styrene, isoprene, acylonitrile, ethyl acrylate, butyl acrylate, maleic acid anhydrate, maleic acid esters, methylmethacrylate, vinyl acrylate, allylmethacrylate, allylsulfonate, vinyl sulfonate, acrylamide, methacrylamide, acrylamidomethylpropanesulfonate (AMPS), $C_1$–$C_4$-hydroxyalkyl methacrylate, $C_1$–$C_4$-hydroxyalkyl acrylate, tripropylene glycol diacrylate, trimethylol propane ethoxylated triacrylate, epoxy acrylates, ethylene oxide, propylene oxide, polyester acrylates, urethane acrylates, $C_1$–$C_{20}$-alkyl methacrylates, vinyl esters of carboxylic acids containing up to 20 carbon atoms, vinyl aromatics having up to 20 carbon atoms, ethylenically unsaturated nitriles, vinyl halides, vinyl ethers of alcohols containing from 1 to 10 carbon atoms, aliphatic hydrocarbons having from 2 to 8 carbon atoms and 1 or two double bonds, and mixtures of these monomers.

Examples of vinyl esters of carboxylic acids having from 1 to 20 carbon atoms are vinyl laurate, vinyl stearate, vinyl propionate, vinyl versatates and vinyl acetate.

Possible vinyl aromatic compounds are vinyl toluene, α- and p-methylstyrene, α-butylstyrene, 4-n-butylstyrene, 4-n-decylstyrene and, preferably, styrene. Examples of nitriles are acrylonitrile and methacrylonitrile.

Vinyl halides are chlorine-, fluorine- or bromine-substituted ethylenically unsaturated compounds, preferably vinyl chloride and vinylidene chloride.

Examples of vinyl ethers, are vinyl methyl ether and vinyl isobutyl ether. Preference is given to vinyl ethers of alcohols containing from 1 to 4 carbon atoms.

As hydrocarbons having from 2 to 8 carbon atoms and two olefinic double bonds, mention should be made of butadiene, isoprene, and chloropene.

The comonomers may also be copolymerized with a precursor molecule of the comonomers. Examples of preferred precursors are vinylformamid, vinylacetate, vinylacetamide, all of which will have to be finally hydrolyzed after the polymerization in order to incorporate the corresponding monomer units, vinylamine and vinylalcohol.

Process

The above-mentioned radiation activatable surface cross-linkers are capable of forming covalent bonds by exposure to electromagnetic irradiation. Electron beams as well as UV-light can produce suitable electromagnetic irradiation. Preferably, according to the present invention UV-light is used with a wave-length of 220–380 nm, depending on the selected radiation activatable surface cross-linker(s). The UV-light may be used in combination with an electron-beam, and also in combination with an IR-light. In case of combination of UV-irradiation with other electromagnetic irradiation, it is not critical if the application of the UV-light takes place simultaneously with the other electromagnetic irradiation (i.e., electron-beam or IR-light), or if irradiation is done in a series of different irradiation steps. For radiation activatable surface cross-linkers, which require a relative high amount of activation energy, activation with electron beams may be necessary.

In the present invention the radiation activatabie surface cross-linker is applied in amounts of less than 50% by weight of SAP particle, preferably in amounts of less than 25%, more preferably in amounts of less than 15%, even more preferably in amounts of less than 5% and most preferably in amounts from 0.1% to 5%.

The novel radiation activatable surface cross-linker may be sprayed onto the SAP particles by means of a fluidized-bed spraying chamber. Simultaneously IR-irradiation may be applied to accomplish drying and simultaneously UV-light may be applied to accomplish cross-linking in the fluidized-bed.

However, in certain cases drying and cross-linking may take place in two steps in series, which could be carried out in any order. Instead or in combination with IR-light, any conventional drying equipment can be used in the drying step. However, in certain embodiments of the present invention little or no drying is required, e.g., in cases, where only small amounts of surface cross-linkers are applied dissolved in small amounts of solution.

The surface cross-linking of the SAP particles with the radiation activatable surface cross-linker according to the present invention effectively takes place at the photo-reactive groups of the radiation activatable surface cross-linker, forming covalent bonds. On exposure to electromagnetic irradiation, most preferably UV-irradiation, a covalent bond is formed by means of the chemical grafting reaction.

In particular, the surface cross-linking may take place upon electromagnetic irradiation by reaction of the activated photo-reactive group of the novel surface cross-linker with an adjacent aliphatic C—H bond, forming a —C—C—O—H group in case the photo-reactive group of the surface cross-linker is a carboxyl group. The aliphatic C—H bond may be part of a nearby polymer chain. This polymer chain may be another radiation activatable surface cross-linker molecule, a part of the same cross-linker molecule or may be part of the SAP particles exposed to the surface of such SAP particles.

Therefore, at least a part of the surface cross-linker molecules form radicals, which are able to react with the functional groups (e.g., carboxyl group) comprised by the polymer and they are also able to react, e.g., with the aliphatic groups comprised by the polymer. As a result of this reaction at least a part of the surface cross-linker molecules are covalently bound to the aliphatic groups comprised by the polymer chains of the SAP particles. Alternatively, it is also possible that the surface cross-linker molecules are covalently bound to at least a part of the carboxyl groups of the polymer chains of the SAP particles. The surface cross-linker will mainly be bound to those carboxyl groups, which are at least partially exposed on the surface of the SAP particles. However, compared to prior art surface cross-linking, the cross-linking process of the present invention is not restricted to the carboxyl groups but also comprises the numerous aliphatic groups within the polymer chains of the SAP. Hence, according to the present invention the number of available reaction sites for the surface cross-linking process of the SAP particles is strongly increased. Therefore, it is possible to achieve a far more homogenous, uniform surface cross-linking compared to the surface cross-linking known from the art. Furthermore, it is possible to surface cross-link the SAP to a higher degree than the SAP known from the prior art. This enables to make the SAP particles much stiffer, thus, to more effectively inhibit the gel-blocking effect at a given degree of neutralization. Moreover, it is possible to increase the capacity of the SAP particles.

As the surface cross-linker is applied on the surface of the SAP particles, the reaction takes mainly place on the surface of the SAP particles. That means, that mainly aliphatic groups and/or functional groups, which are exposed in the vicinity of the surface of the SAP particles, undergo a cross-linking process, leading to SAP particles with a high degree of cross-linking on their surface while not substantially affecting the inner core (=interior portion) of the SAP particles. Hence, the percentage of the reaction product of the radiation activatable surface cross-linker on the surface of said superabsorbent polymer particles will preferably be higher than the percentage of the reaction product of the radiation activatable surface cross-linker inside the superabsorbent polymer particles.

The UV irradiation for the surface cross-linking can preferably be carried out in a conventional manner with UV lamps having a power between 50 W and 2 kW, more preferably between 200 W and 700 W, and even more preferred between 400 W and 600 W. Irradiation time is preferably between 0.1 sec. and 30 min., more preferably between 0.1 sec. and 15 min, even more preferably between 0.1 sec. and 5 min and most preferably between 0.1 sec. and 2 min. Commercially available mercury pressure UV-lamps can be used. The choice of the lamp depends on the absorption spectrum of the radiation activatable surface cross-linker(s) used. Lamps having a higher power generally permit more rapid cross-linking. The distance between the UV-lamp(s) and the SAP which is to be cross-linked preferably varies between 5 cm and 15 cm.

Compared to the surface cross-linking known from the prior art, the surface cross-linking according to the present invention is much quicker. Prior art surface cross-linking reactions carried out under increased temperatures commonly take up to 45 minutes. This time consuming process step renders the manufacturing process of SAP particles less economic than desirable. On the contrary, the cross-linking process according to the present invention can be carried out very quickly and hence, strongly adds to a much more efficient and economic overall manufacturing process.

Furthermore, as the surface cross-linking reaction proceeds quickly, the surface cross-linking molecules applied on the surface of the SAP particles have less time to penetrate inside the SAP particles. As a result, the surface cross-linking process is mainly restricted to the surface of the SAP particles and avoids undesired further cross-linking reactions inside the SAP particles.

Another advantage of the present invention refers to the neutralization step. The $\alpha,\beta$-unsaturated carboxylic acid monomers are often neutralized prior to the polymerization step (pre-neutralization). Compounds, which are useful to neutralize the acid groups of the monomers, are typically those, which will sufficiently neutralize the acid groups without having a detrimental effect on the polymerization process. Such compounds include alkali metal hydroxides, alkali metal carbonates and bicarbonates. Preferably, the material used for neutralization of the monomers is sodium or potassium hydroxide or carbonate. The neutralizing compound is preferably added to an aqueous solution comprising the $\alpha,\beta$-unsaturated carboxylic acid monomers (pre-neutralization). As a result, the carboxyl groups comprised by the $\alpha,\beta$-unsaturated carboxylic acid monomers are at least partially neutralized. Consequently,—after the polymerization step—also the carboxyl groups comprised by the $\alpha,\beta$-unsaturated carboxylic acid of the polymer are at least partially neutralized. In case sodium hydroxide is used, neutralization results in sodium acrylate, which dissociates in water into negatively charged acylate monomers and positively charged sodium ions.

If the final SAP particles are in the swollen state, after they absorbed aqueous solution, the sodium ions are freely movable within the SAP particles. In absorbent articles, such as diapers or training pants, the SAP particles typically absorb urine. Compared to distilled water, urine comprises a relatively high amount of salt, which at least partly is present in dissociated form. The dissociated salts comprised by the urine make absorption of liquid into the SAP particles more difficult, as the liquid has to be absorbed against an osmotic pressure caused by the ions of the dissociated salts. The freely movable sodium ions within the SAP particles strongly facilitate the absorption of liquid into the particles, because they reduce the osmotic pressure. Therefore, a high degree of neutralization can largely increase the capacity of the SAP particles and the speed of liquid absorption.

The surface cross-linkers known in the art react with the carboxyl groups of the polymer. Hence, the degree of neutralization has to be balanced with the need to surface cross-link, because both process steps make use of the carboxyl groups.

According to the present invention, the surface cross-linker comprises radiation activatable groups and—once activated, e.g., by UV irradiation—it is able to react not only with the carboxyl groups but also with the aliphatic groups comprised by the polymer. Therefore, it is possible to neutralize the monomers to a larger degree without significantly diminishing the possibility of later surface cross-linking.

According to the present invention, the carboxyl groups comprised by the $\alpha,\beta$-unsaturated carboxylic acid monomers are preferably at least 50%, more preferably at least 70%, even more preferably at least 75% and even more preferably between 75% and 95% neutralized. Hence, also the carboxyl groups comprised by the $\alpha,\beta$-unsaturated carboxylic acid of the polymer are at least 50%, more preferably at least 70%, even more preferably at least 75% and even more preferably between 75% and 95% neutralized.

A still further advantage of the present invention is the reduction of undesired side-reactions during the surface cross-linking process. Surface cross-linking known from the prior art requires increased temperatures, commonly around or above 150°. At these temperatures, not only the surface cross-linking reaction is achieved, but also a number of other reactions take place, e.g., anhydride-formation within the polymer or dimer cleavage of dimers previously formed by the acrylic acid monomers. These side-reactions are highly undesired, because they result in SAP particles with decreases capacity.

As the surface cross-linking process according to the present invention does not necessarily need increased temperatures but can also be carried out at moderate temperatures using electromagnetic irradiation, such as UV irradiation, those side-reactions are considerably reduced. According to the present invention, the surface cross-linking reaction can preferably be accomplished at temperatures of less than 100° C., preferably at temperatures less than 80° C., more preferably at temperatures less than 50° C., even more preferably at temperatures less than 40° C., most preferably at temperatures between 20° C. and 40° C. In an additional process step drying of the SAP is typically carried out at temperatures above 100° C.

At elevated temperatures around or above 150° C. commonly applied in the surface cross-linking process known from the prior art, the SAP particles sometimes change their color from white to yellowish. As according to the surface cross-linking process of the present invention, it is possible to carry out the surface cross-linking process under moderate temperatures, the problem of color degradation of the SAP particles is strongly reduced.

According to the present invention, one surface cross-linker can be selected or, alternatively, two or more different surface cross-linkers, can be applied, all being radiation activatable surface cross-linkers.

As a further alternative, one or more surface cross-linkers being radiation activatable surface cross-linker(s) can be applied together with one or more thermally activatable surface cross-linkers, e.g., 1,4-butandiol. In this embodiment, the SAP particles further have to comprise carboxyl groups wherein at least some of the carboxyl groups are at least partially exposed on the outer surface of the SAP particles and wherein the thermally activated surface cross-linker is covalently bound to at least a part of the carboxyl groups at least partially exposed on the surface of said superabsorbent polymer particles.

In case a radiation activatable surface cross-linker is used together with a thermally activatable surface cross-linker, both UV irradiation and increased temperatures (above 140° C.) are necessary for the surface cross-linking process.

The radiation activatable surface cross-linker is preferably used in a liquid solution, more preferably in an aqueous solution.

To obtain SAP particles with evenly distributed surface cross-linking, the surface cross-linker has to be distributed evenly on the SAP particle prior to or during UV irradiation. Therefore, the surface cross-linker is preferably applied by spraying onto the SAP particles.

Absorbent Articles

The SAP particles of the present invention are preferably applied in absorbent articles. As used herein, absorbent article refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, diaper holders and liners, sanitary napkins and the like.

Preferred absorbent articles of the present invention are diapers. As used herein, "diaper" refers to an absorbent article generally worn by infants and incontinent persons about the lower torso.

"Disposable" is used herein to describe articles that are generally not intended to be laundered or otherwise restored or reused, i.e., they are intended to be discarded after a single use and, preferably, to be recycled, composted or otherwise disposed of in an environmentally compatible manner.

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis 22 may also include most or all of the absorbent core 28 encased between the topsheet 24 and the backsheet 26. The chassis 22 preferably further includes side panels 30, leg cuffs 32 with elastic members 33 and a waist feature 34. The leg cuffs 32 and the waist feature 34 typically comprise elastic members. One end portion of the diaper is configured as the front waist region 36 of the diaper 20. The opposite end portion is configured as the rear waist region 38 of the diaper 20. The intermediate portion of the diaper is configured as the crotch region 37, which extends longitudinally between the front and rear waist regions. The crotch region 37 is that portion of the diaper 20 which, when the diaper is worn, is generally positioned between the wearer's legs.

The waist regions 36 and 38 may include a fastening system comprising fastening members 40 preferably attached to the rear waist region 38 and a landing zone 42 attached to the front waist region 36.

The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

The diaper may also include other features as are known in the art including front and rear ear panels, waist cap features, elastics and the like to provide better fit, containment and aesthetic characteristics.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, absorbent gelling materials, or any other known absorbent material or combinations of materials. The absorbent core may further comprise minor amounts (typically less than 10%) of non-liquid absorbent materials, such as adhesives, waxes, oils and the like.

Furthermore, the SAP particles of the present invention can be applied as absorbent materials. The SAP particles of the present invention preferably are present in amounts of at least 50% by weight of the whole absorbent core, more preferably at lest 60%, even more preferably at least 75% and still even more preferably at least 90% by weight of the whole absorbent core.

FIG. 2 shows a cross-sectional view of FIG. 1 taken in the transverse axis 110. FIG. 2 illustrates a preferred embodiment of the different zones comprised by the absorbent cores. In FIG. 2, the fluid acquisition zone 50 comprises an upper acquisition layer 52 and a lower acquisition layer 54, while the fluid storage zone underneath the fluid acquisition zone comprises a storage layer 60, which is wrapped by an upper core wrap layer 56 and a lower core wrap layer 58.

In one preferred embodiment the upper acquisition layer 52 comprises a nonwoven fabric whereas the lower acquisition layer 54 preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer.

In a preferred embodiment the core wrap material comprises a top layer 56 and a bottom layer 58, which layers may be sealed together along their edges, e.g., by adhesive. The top layer 56 and the bottom layer 58 can be provided from a non-woven material. The top layer 56 and the bottom layer 58 may be provided from two or more separate sheets of materials or they may be alternatively provided from a unitary sheet of material. Such a unitary sheet of material may be wrapped around the storage layer, e.g., in a C-fold.

The storage layer 60 in the present invention typically comprises SAP particles mixed with fibrous materials. Other materials as suitable for the absorbent core may also be comprised.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Superabsorbent polymer particles comprising a water-absorbing resin that has been reacted with a radiation activatable surface cross-linker wherein the reaction product of the radiation activatable surface cross-linker and the water absorbing resin is present at surfaces of the superabsorbent polymer particles, wherein said radiation activatable surface cross-linker comprises at least two radiation activatable groups R, said at least two radiation activatable groups R being covalently bound to each other or to at least one spacer group S, wherein the spacer group S is a spacer group selected from the group consisting of an organic group with a molecular weight of up to about Mw=10000, and a polymeric group with a molecular weight of up to about Mw=1000000, and wherein said radiation activatable groups R are the same or different and are selected from the group consisting of:
   a) acetophenone, benzophenone, anthraquinone, xanthone, thioxanthone, camphorquinone, terephthalophenone benzil, fluorenone, -ketocoumarin and acetophenone-, benzophenone-, anthraquinone-, xanthone-, thioxanthone-, camphorquinone-, terephthalophenone-, benzil-, fluorenone-, and -ketocoumarin-derivatives, wherein acetophenone derivatives and benzophenone derivatives also comprise condensation products of acetophenone derivatives or benzophenone derivatives, comprising at least two acetophenone or benzophenone groups, and
   b) a group comprising a first group selected from the group consisting of methyl, benzyl, aryl, phenyl and substituted phenyl, and a second group selected from the group consisting of an aryl, an alkyl of 1 to 4 carbon atoms, cyclopropyl, cyclopentyl, cyclohexyl, α,α-dialkoxyalkyl, and α-hydroxyalkyl and wherein said first group is covalently bound to said second group via an additional carbonyl group therebetween, and wherein the second group is covalently bound to said spacer group S or to another radiation activatable group.

2. Superabsorbent polymer particles according to claim 1, wherein said superabsorbent polymer particles comprise homopolymers of partially neutralized α,β-unsaturated carboxylic acid or copolymers of partially neutralized α,β-unsaturated carboxylic acid copolymerized with a monomer copolymerizable therewith, said homopolymers or said copolymers comprising aliphatic groups, wherein at least some of said aliphatic groups are at least partially exposed on the surface of said superabsorbent polymer particles and wherein said reaction product of the radiation activatable surface cross-linker is covalently bound to at least a part of the aliphatic groups at least partially exposed on the surface of said superabsorbent polymer particles.

3. Superabsorbent polymer particles according to claim 1, wherein said superabsorbent polymer particles comprise about 100 parts by weight of said water absorbing resin and less than about 50 parts by weight of said radiation activatable surface cross-linker.

4. Superabsorbent polymer particles according to claim 1, wherein said superabsorbent particles comprise said reaction product on said surface and in an interior portion of said superabsorbent particles, wherein the percentage of said reaction product of the radiation activatable surface cross-linker on said surface of said superabsorbent polymer particles is higher than the percentage of said reaction product in the interior portion of said superabsorbent polymer particles.

5. Superabsorbent polymer particles according to claim 1, wherein said radiation activatable groups R are defined by the following Formula:

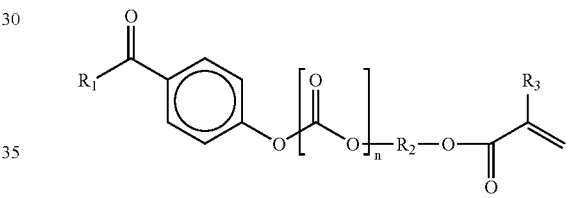

wherein n is 0 or 1, and
   $R_1$ is selected from: substituted phenyls, unsubstituted phenyls, $C_1$–$C_4$-alkyls, an ethylenically unsaturated group, acrylic groups, and methacrylic groups, and
   $R_2$ is an organic group having from 1 to 100 carbon atoms, which may be interrupted by up to 49 oxygen atoms, and
   $R_3$ is selected from a hydrogen atom and a methyl group.

6. Superabsorbent polymer particles according to claim 1, wherein said superabsorbent polymer particles comprise at least two different reaction products of radiation activatable surface cross-linkers.

7. An absorbent article comprising a substantially liquid pervious topsheet, a substantially liquid impervious backsheet and an absorbent core between said topsheet and said backsheet, wherein said absorbent article comprises superabsorbent polymer particles according to claim 1.

8. An absorbent article comprising superabsorbent polymer particles according to claim 1.

* * * * *

UNITED STATES PATENT AND TRADEMARK OFFICE
CERTIFICATE OF CORRECTION

| | | |
|---|---|---|
| PATENT NO. | : 7,166,356 B2 | Page 1 of 1 |
| APPLICATION NO. | : 10/911302 | |
| DATED | : January 23, 2007 | |
| INVENTOR(S) | : Andreas Flohr | |

It is certified that error appears in the above-identified patent and that said Letters Patent is hereby corrected as shown below:

Column 11
Line 65, delete "activatabie" and insert -- activatable --.

Signed and Sealed this

Fourth Day of September, 2007

JON W. DUDAS
*Director of the United States Patent and Trademark Office*